US009387235B2

(12) United States Patent
Moussou et al.

(10) Patent No.: US 9,387,235 B2
(45) Date of Patent: Jul. 12, 2016

(54) COSMETIC PREPARATIONS CONTAINING PTH FRAGMENTS

(75) Inventors: Philippe Moussou, Tomblaine (FR); Louis Danoux, Saulxures les Nancy (FR); Vincent Bardey, Nancy (FR); Christine Jeanmaire, Nancy (FR); Gilles Pauly, Nancy (FR)

(73) Assignee: BASF Beauty Care Solutions France S.A.S., Lyon (FR)

( * ) Notice: Subject to any disclaimer, the term of this patent is extended or adjusted under 35 U.S.C. 154(b) by 621 days.

(21) Appl. No.: 11/570,614

(22) PCT Filed: Jun. 6, 2005

(86) PCT No.: PCT/EP2005/006261
§ 371 (c)(1),
(2), (4) Date: Aug. 6, 2007

(87) PCT Pub. No.: WO2005/120554
PCT Pub. Date: Dec. 22, 2005

(65) Prior Publication Data
US 2011/0059892 A1     Mar. 10, 2011

(30) Foreign Application Priority Data

Jun. 14, 2004   (EP) ...................... 04291496

(51) Int. Cl.
| | | |
|---|---|---|
| *A61K 38/00* | (2006.01) | |
| *C07K 16/00* | (2006.01) | |
| *A61K 38/29* | (2006.01) | |
| *A61K 8/64* | (2006.01) | |
| *A61K 38/07* | (2006.01) | |
| *A61Q 7/00* | (2006.01) | |
| *A61Q 19/06* | (2006.01) | |
| *A61Q 19/08* | (2006.01) | |

(52) U.S. Cl.
CPC . *A61K 38/29* (2013.01); *A61K 8/64* (2013.01); *A61K 38/07* (2013.01); *A61Q 7/00* (2013.01); *A61Q 19/06* (2013.01); *A61Q 19/08* (2013.01)

(58) Field of Classification Search
CPC ...... C07K 5/125; C07K 14/705; A61K 38/07; A61K 35/12
See application file for complete search history.

(56) References Cited

U.S. PATENT DOCUMENTS

| | | | |
|---|---|---|---|
| 4,172,887 A | 10/1979 | Vanlerberghe et al. | |
| 5,037,643 A | 8/1991 | Green | |
| 5,958,384 A * | 9/1999 | Holick | ............ 424/60 |
| 6,110,892 A * | 8/2000 | Barbier et al. | ........... 514/11.8 |
| 6,337,315 B1 | 1/2002 | Mahe et al. | |
| 6,541,450 B1 * | 4/2003 | Barbier et al. | ........... 514/11.8 |
| 6,756,480 B2 * | 6/2004 | Kostenuik et al. | ........ 530/387.1 |
| 7,211,269 B2 * | 5/2007 | Dal Farra et al. | ........... 424/401 |
| 7,282,484 B2 * | 10/2007 | Wallner et al. | ........... 514/19.4 |
| 2003/0017969 A1 * | 1/2003 | Tennenbaum et al. | .......... 514/3 |
| 2005/0026845 A1 | 2/2005 | Mahe et al. | |
| 2007/0117157 A1 | 5/2007 | Zajac | |

FOREIGN PATENT DOCUMENTS

| | | |
|---|---|---|
| DE | 197 56 377 | 6/1999 |
| FR | 2252840 | 6/1975 |
| JP | 2000-080024 | 3/2000 |
| JP | 1-287013 | 10/2001 |
| JP | 2003-300823 | 10/2003 |
| JP | 2004-059478 | 2/2004 |
| JP | 2004-536018 | 12/2004 |
| JP | 2006-517086 | 7/2006 |
| JP | 9-124502 | 6/2009 |
| WO | WO 00/04047 | 1/2000 |
| WO | WO 00/40611 | 7/2000 |
| WO | WO 02/09639 | 2/2002 |

OTHER PUBLICATIONS

Jouishomme et. al. Further Definition of the Protein Kinase C Activation Domain of the Parathyroid Hormone, Journal of Bone and Mineral Research. vol. 9, No. 6, 1994 p. 843 Col. 1-Col. 2.*
Parathyroid Hormone and Parathyroid Hormone Related Peptide Inhibit the Apical Na+/H+ Exchanger NHE-3 Isoform in Renal Cells (OK) via Dual Signaling Cascade Involving Protein Kinase A and C, The Journal of Biological Chemistry vol. 270, No. 34 Aug. 25 pp. 20004-20010 (1995).*
Azrani et. al. Parathyroid Hormone and Parathyroid Hormone Related Peptide Inhibit the Apical Na+/H+ Exchanger NHE-3 Isoform in Renal Cells (OK) via Dual Signaling Cascade Involving Protein Kinase A and C, The Journal of Biological Chemistry vol. 270, No. 34 Aug. 25th pp. 20004-20010 (1995).*
Jouishomme et al. (Further Definition of the Protein Kinase C Activation Domain of the Parathyroid Hormone, Journal of Bone and Mineral Research, vol. 9, No. 6, 1994.*
The Free Medical Dictionary, http://medical-dictionary.thefreedictionary.com/derivative, last visited Jun. 15, 2013.*

(Continued)

*Primary Examiner* — Jeanette Lieb
(74) *Attorney, Agent, or Firm* — Servilla Whitney LLC

(57) ABSTRACT

A cosmetic or pharmaceutical composition includes a peptide parathyroid hormone fragment, derivatives thereof, salts thereof, and combinations thereof, where the peptide fragment conforms to the structure

R1-NH-AA-R2 where R1 is selected from the group consisting of —H, a linear or branched, saturated or unsaturated acyl group having from 1 to 24 carbon atoms optionally functionalized with an —OH, —SH, —COOH or —CONH2 group, or a sterol group which is bonded by a functional group with the peptide; where R2 is —OH, —OH functionalized by a linear or branched, saturated or unsaturated alkyl group having from 1 to 24 carbon atoms, or a sterol group; and where AA corresponds completely or partially to the sequence of amino acids according to SEQ ID No. 1 corresponding to the PTH (28 to 34) region.

13 Claims, No Drawings

(56) References Cited

OTHER PUBLICATIONS

Jouishomme et. al. Further Definition of the Protein Kinase C Activation Domain of the Parathyroid HormoneJ. Bone Mineral Res. vol. 9 (1994).*

Forenske, J Am Acad Dermatol. Oct. 1986;15(4 Pt 1):571-85.*

Cataisson et al. The Journal of Immunology, 2003, 171: 2703-2713.*

Holick et al., "A parathyroid hormone antagonist stimulates epidermal proliferation and hair growth in mice," Proceedings of the Natl. Academy of Science, 1994, vol. 91, pp. 8014-8016, XP002213035.

Wu et al., "Parathyroid Hormone Regulates Transforming Growth Factor beta1 and beta 2 Synthesis in Osteoblasts Via Dlvergent Signaling Pathways", J. ofBoneAndMineralResearch, 2000, vol. 15—pp. 879-884, XP-009053051.

Jouishomme et al., "Further Definition of the Protein Kinase C Activation Domain of the Parathyroid Hormone", J.ofBoneAndMineralResearch, 1994, vol. 9, pp. 943-949, XP-009053052.

Kim et al., "Effect of Topical Retinoic Acids on the Levels of Collagen mRNA During the Repair of UVB-Induced Dermal Damage in the Hairless Mouse and the Possible Role of TGF-BETA as a Mediator", J.ofinvestigative Dermatology, 1992, vol. 98, pp. 359-363, XP-000889815.

Jouishomme at al., "The Protein Kinase-C Activation Domain of the Parathyroid Hormone", Endocrinology, 1992, vol. 130, pp. 53-60.

Lochhead et al., "Encyclopedia of Polymers and Thickeners for Cosmetics", Cosmetics&Toiletries, 1993, vol. 108, pp. 95-136.

Kosmetische Faerbemittal, Deutsche Forschungsgemeinschaft, 1984, Edition Chemie, pp. 81-106.

Hisaya, Asumi "Machine Translation of JP2004059478", Feb. 26, 2004, 1-1.

Tanaka, Hiroshi "Machine Translation of JP2003300823", Oct. 21, 2003, 1-1.

Maioli, E., et al., "Effect of parathyroid hormone-related protein on fibroblast proliferation and collagen metabolism in human skin", *Experimental Dermatology 11* 2002, 302-310.

Thomson, M., et al., "Parathyroid hormone-related peptide modulates signal pathways in skin and hair follicle cells", *Experimental Dermatology 12* 2003, 389-395.

Whitfield, James F. et al., "C-Terminal Fragment of Parathyroid Hormone-Related Protein, PTHrP-(107-111), Stimulates Membrane-Associated Protein Kinase C Activity and Modulates the Proliferation of Human and Murine Skin Keratinocytes", *Journal of Cellular Physiology 166* 1996, 1-11.

Newton, Alexandra C., "Protein Kinase C: Structure, Function, and Regulation", *The Journal of Biological Chemistry*, vol. 270, No. 48 1995, 28495-28498.

Breitkreutz, D. et al., "Protein kinase C family: On the crossroads of cell signaling in skin and tumor epithelium", *J Cancer Res Clin Oncol* 2007, 16 pgs.

* cited by examiner

COSMETIC PREPARATIONS CONTAINING PTH FRAGMENTS

CROSS-REFERENCE TO RELATED APPLICATIONS

This application is the national phase under 35 U.S.C. §371 of PCT International Application No. PCT/EP2005/006261 which has an International filing date of Jun. 6, 2005, which designated the United States of America and which claims priority on European Patent Application number EP 04291496.0 filed Jun. 14, 2004, the entire disclosures of which are hereby incorporated herein by reference.

FIELD OF THE INVENTION

The present invention relates to cosmetic preparations which contain fragments of parathyroid hormone PTH. The present invention also relates to the use of cosmetic preparations containing peptide fragments of parathyroid hormone PTH in cosmetic or pharmaceutical fields of application.

BACKGROUND INFORMATION

Cosmetic preparations are nowadays available to consumers in a large number of combinations. Consequently, it is not only expected that those cosmetics have a specific beneficial effect or that they remedy a given deficiency, but increasingly it is expected of the products that they have at the same time a plurality of properties, and consequently that they have a wider scope of effectiveness. Substances which positively influence the technical properties of the cosmetic product, such as stability during storage, light-resistance and the capacity for formulating them, and substances which have at the same time active ingredients which provide the skin and hair, for example, with beneficial anti-irritant and anti-inflammatory properties and/or properties providing protection against light. Here, customers further demand that the product be well-tolerated by the epidermis and that, in particular, natural products be used.

There is a need for effective protection of the skin against the harmful influences of the environment.

Cosmetic preparations containing peptides with a large number of amino acids, such as, for example, complete parathyroid hormone PTH (84 amino acids) or PTH fragment (1 to 34) cannot be used and can also be implemented only partially, the production of that type of peptide being extremely expensive and difficult on an industrial scale.

In document WO 00/40 611 and document WO 00/04 047, the use of peptides in cosmetics and dermatology is described in relation to weight-loss products having topical applications. Those peptides display a lipolytic activity on the activity of the adenylate cyclase membrane. Specific fragments of parathyroid hormone PTH are described as active peptides. These are PTH (1 to 6), PTH (1 to 10), PTH (9 to 19) and preferably PTH (12 to 16) and PTH (12 to 14).

The PTH region (28 to 34) Leu-Gln-Asp-Val-His-Asn-Phe has been able to be identified as a stimulator of the protein kinase C (PKC) in osteosarcoma cells of ROS 17/2 rats [Jouishomme H. et al. The protein kinase-C activation domain of the parathyroid hormone Endocrinology 130: 53-60 (1992)]. The same research group has also discovered that the minimum domain of PTH in a position to function fully in the activation of PKC represents region 29 to 32 (Gln-Asp-Val-His) and that an exchange of polar amino acid His with non-polar acid Leu does not negatively influence the activation of PKC (Jouishomme et al. Further definition of the protein kinase C activation domain of the parathyroid hormone. J. Bone miner Res. 9: 943-9 (1994)).

SUMMARY OF THE INVENTION

Briefly described, according to an aspect of the invention, a cosmetic or pharmaceutical composition includes a peptide parathyroid hormone fragment, derivatives thereof, salts thereof, and combinations thereof, wherein the peptide fragment conforms to the structure

R1-NH-AA-R2 where R1 is selected from the group consisting of —H, a linear or branched, saturated or unsaturated acyl group having from 1 to 24 carbon atoms optionally functionalized with an —OH, —SH, —COOH or —CONH2 group, or a sterol group which is bonded by a functional group with the peptide; where R2 is —OH, —OH functionalized by a linear or branched, saturated or unsaturated alkyl group having from 1 to 24 carbon atoms, or a sterol group; and where AA corresponds completely or partially to the sequence of amino acids according to SEQ ID No. 1 corresponding to the PTH (28 to 34) region.

According to another aspect of the invention, a cosmetic preparation includes a derivative of peptide fragments of parathyroid hormone which conforms to the structure

R1-NH-AA-R2 where R1 is selected from the group consisting of H, a linear or branched, saturated or unsaturated acyl group having from 1 to 24 carbon atoms, optionally functionalized with an —OH, —SH, —COOH or —CONH2 group, or a sterol group which is bonded by a functional group with the peptide, where R2 is —OH, —OH functionalized by a linear or branched, saturated or unsaturated alkyl group having from 1 to 24 carbon atoms, or a sterol group; where AA corresponds completely or partially to the amino acid sequence according to SEQ ID No. 1 of PTH (28-34) region, with the proviso that R1 is H when R2 is different from OH, or R1 is different from H when R2 is OH.

DETAILED DESCRIPTION OF THE INVENTION

An object of the present patent application was to provide cosmetic preparations which provide protection for the skin, the scalp, the mucous membrane and/or the hair against the aggressive effects of the environment, oxidising stress, toxic substances or UV rays, and which contribute in particular to retarding ageing of the skin and healing and, consequently, which can be used effectively in cosmetics and dermopharmacology for topical application.

Another object of the present invention consists in providing cosmetic preparations with the profile mentioned which contain peptide fragments which are as short as possible and effective, or derivatives of peptide fragments.

In a surprising manner, it has now been discovered that a cosmetic preparation containing the peptide fragment of PTH (28 to 34) corresponding to SEQ ID No. 1 or the peptide fragment (29 to 32) (Gln-Asp-Val-His) corresponding to the 2 to 5 positions of SEQ ID No. 1 satisfied the requirements set.

Consequently, a first object of the present application relates to the use of peptide fragments and/or derivatives and/or salts of peptide fragments of parathyroid hormone which comply with the structure

R1-NH-AA-R2 where R1 is selected from the group which is formed by —H, the linear, saturated or unsaturated acyl group or branched, saturated or unsaturated acyl group having from 1 to 24 carbon atoms which can be functionalized with an —OH, —SH, —COOH or —CONH2 group, or a sterol group which is bonded by a functional group, such as a diacid with the peptide;

where R2=—OH or the OH group is functionalized by a linear saturated or unsaturated alkyl group or branched saturated or unsaturated alkyl group having from 1 to 24 carbon atoms or a sterol group;

where AA corresponds completely or partially to the sequence of amino acids according to SEQ ID No. 1 corresponding to the PTH region (28 to 34) (Leu-Gln-Asp-Val-His-Asn-Phe), in particular the PTH region (29 to 32) corresponding to position 2 to 5 of SEQ ID No. 1 (Gln-Asp-Val-His);

in order to produce a cosmetic and/or pharmaceutical preparation or in order to treat, in cosmetic terms, the skin and human hair against intrinsic or extrinsic, cutaneous deterioration, and in order to prevent the appearance of deterioration.

The residue R1 is preferably selected from the group which is formed by the acetyl group, the ethanoyl group, the propionyl group, the butanoyl group, the decanoyl group, the palmitoyl group, the stearoyl group, the oleyl group, the lipoyl group, the linoleyl group or the conjugated linoleyl group, the acetyl group being preferred in particular.

The sterol group preferably comprises cholesterol, stigmasterol, sitosterol, brassicasterol or sphingolipid, which group is bonded by a functional group, such as a diacid, for example, a succinic acid.

When R2 represents a sterol group, it is preferably selected from the group formed by cholesterol, stigmasterol, sitosterol, brassicasterol or sphingolipid.

The sequence of amino acids AA which corresponds completely or partially to the sequence of amino acids according to SEQ ID No. 1, is preferably position 2 to 5 of SEQ ID No. 1 corresponding to the PTH (29 to 32) region (Gln-Asp-Val-His) or is preferably composed of pGlu-Asp-Val-His (SEQ ID NO:2).

In a preferred embodiment of the invention, R1 denotes H or an acetyl group and R2=OH, where it is particularly preferable for, in the same manner, AA to represent position 2 to 5 of SEQ ID No. 1 corresponding to the PTH region (29 to 32).

In another specific embodiment of the present invention, the sequence of amino acids according to SEQ ID No. 1 or the preferred position 2 to 5 of SEQ ID No. 1 corresponding to the PTH region (29 to 32) may be replaced, His being replaced by an amino acid selected from the group comprising Leu, Ile, Nle (Norleucine), Met, Val, Ala, Trp or Phe.

According to the present invention, the peptide fragments are obtained by chemical or enzymatic synthesis and by controlled hydrolysis of natural proteins of micro-organisms, plants or animals which contain the sequence according to SEQ ID No. 1. The hydrolysate containing the sequence according to SEQ ID No. 1 or at least position 2 to 5 of SEQ ID No. 1, corresponding to the PTH region (29 to 32) obtained by hydrolysis of the natural proteins can be purified by known techniques, such as filtration over a membrane, chromatography or immunoprecipitation. The peptide fragments may also be produced by micro-organisms which form the peptide fragments naturally or, optionally, they could be modified genetically, or they are also manipulated by other means during fermentation by fermentation conditions which form the peptide fragments according to the present invention.

Amino acids may be produced in the form L or D or DL in a peptide fragment.

In a preferred embodiment, the peptide fragments, derivatives and/or salts of peptides fragments according to the present invention are used to produce a preparation which is effective for combating the formation of wrinkles and for reducing the impressions left behind by wrinkles or for strengthening the dermis and/or the dermis/epidermis junction (DEJ) or for reducing the phenomenon of cellulite of the sub-cutaneous tissues or for promoting healing or for combating the reduction in the number of cells brought about by deterioration of human skin or for stimulating and/or regenerating capillary re-growth and combating the loss of hair.

Peptide fragments and/or fragment derivatives and/or fragment salts are preferentially used, according to the present invention as component of a preparation, that is efficient to stimulate the production of TGFβ1 protein (transforming growth factor) and/or its receptors present at the cell surface that initiate a biological response to the TGFβ1 or to stimulate the production of mRNAs and proteins of the extra-cellular matrix such as collagen, elastin and/or proteoglycanes such as lumican and syndecan or to fight against inflammation.

Peptide fragments and/or fragment derivatives and/or fragment salts are preferentially used, according to the present invention as component of a preparation, that is efficient to stimulate the production of mRNAs and proteins such as perlecan, thrombospondin, nidogen, or integrins, or to regulate the rate of proteins involved in the degradation of the extra-cellular matrix, such as MMP2 and/or MMP9, and/or to control expression of TIMPs (tissue inhibitors of metalloproteinase).

Intrinsic factors which trigger genetic modifications, or extrinsic factors which are conditioned by environmental conditions, such as UV radiation, oxidising stress, toxic pollutants, lead to premature ageing of the skin and increase the occurrence of cutaneous ageing, such as, for example, wrinkles.

The reduction in the impression left behind by wrinkles relates both to the depth of the wrinkles and to their length.

Skin modifications induced by ageing are characterised by a reduction of thickness of dermal and epidermal skin layers, due to a modification of the extra-cellular matrix, composed of four types of macromolecules: collagen, elastin, glycoproteins and proteoglycans. These modifications are due to a reduction of the proliferation of keratinocytes and fibroblasts, and to a decreased production of extracellular matrix proteins and to an increased synthesis of metalloproteinases (MMP), enzymes involved in the degradation of the matrix.

Using peptide fragments and/or fragment derivatives and/or fragment salts of peptides of parathyroid hormone, according to the SEQ ID No. 1, preferentially equal to the position 2-5 of the SEQ ID No. 1, which is equivalent to the domain PTH (29-32), as component of cosmetic and/or pharmaceutical preparations, allows to obtain preparations, that efficiently increase the number of human aged skin cells and that efficiently stimulate production of mRNAs and proteins, such as collagen, elastin, proteoglycanes. These preparations also efficiently stimulate synthesis of perlecan, thrombospondin, nidogen and/or integrins, that are involved in the synthesis of dermo-epidermal junction, and may also be implicated in the control of matrix degradation enzymes, such as MMP2 and/or MMP9 and/or in the control of TIMPs.

Different studies have shown that skin dermo/epidermal junction was altered by ageing or UV radiation.

The DEJ separates the epidermis and its dependent tissues from the dermis and has a complex structure which comprises hemidesmosomes, intermediary filaments, anchoring filaments, the lamina densa and anchoring fibrillae. The biological components mainly formed at that point include laminine-5 in the lamina lucida; antigens AgBP 230 and AgPB 180 and plectine/HD1 in the hemidesmosomes; entactine/nidogene and proteoglycan, perlecan in the lamina lucida and lamina densa; type IV collagen in the lamina densa and type VII collagen as a component of the anchoring fibrillae in the sub-lamina densa. All these components are involved in an interacting network. When the skin deteriorates, a general weakening of the junctions is brought about and leads to reduced effectiveness of the junctions.

The function of the DEJ is an essential condition not only for health but also for outward appearance. It ensures good cohesion between the epidermis and the subjacent tissues of the dermis, and it also provides the resilience and firmness of the skin and prevents the formation of wrinkles. Consequently, the DEJ ensures good irrigation of the skin, on the one hand, owing to the circulation of vital molecules between the epidermis and the dermis and, on the other hand, protection against the penetration of harmful molecules into the cutaneous, deeper layers.

Conditioned by the improvement in the transit function of the molecules, the exchange between the keratinocytes and the dermis and the supply of the skin are optimised, and consequently, not only is the skin protected against ageing, but also against the harmful influences of UV rays and the toxic influences of the environment, better irrigation also reinforcing the defence against harmful molecules.

In the scalp, the DEJ surrounds the hair follicles and provides at that point protection for the follicle so that reinforcement of the DEJ in that region brings about an improvement in the properties of the hair, and in particular combats the loss of hair or deterioration in the capillary structure.

Peptide fragments and/or fragment derivatives and/or fragment salts of peptides of parathyroid hormone, according to the SEQ ID No. 1, preferentially equal to the position 2-5 of the SEQ ID No. 1, which is equivalent to the domain PTH (29-32), are preferentially used, according to the present invention as component of an efficient preparation, to stimulate the production of TGFβ1 protein and/or its receptors present at the cell surface that initiate a biological response to the TGFβ1.

It has been possible to demonstrate that peptide fragments of the PTH stimulated the growth of cultivated human dermis fibroblasts. Stimulation of cellular proliferation may be due to an increase of the production of TGFβ1 mRNAs and proteins. A stimulation of latent transforming growth factor beta binding proteins or of the TGFR3 receptor located at the cell surface may also be realised.

Among the growth factors, TGFβ1 is one of the most effective regulators of cell metabolism and it takes part in the induction of the synthesis of CTGF (Connective tissue growth factor), FGF-2 (fibroblast growth factor 2) and the matrix proteins. The induction of the synthesis of the growth factors CTGF and FGF-2, as well as other matrix proteins, is also stimulated by TGFβ1 when the present invention is used.

It is known that TGFβ1 promotes synthesis of the cutaneous components of the extracellular matrix, such as collagen. For that reason, it reinforces the resilience and resilient tension of the dermis and acts against the appearance of cellulite, which is brought about by an increase in adipose sub-cutaneous tissue. It is further known that TGFβ1 has a number of functions and that it contributes to the inhibition of growth of cells which are responsible for inflammation. The inflammation process is inhibited and TGFβ1 reduces the inflammation after an injury and consequently contributes to better healing.

Use according to the present invention is characterised in that the peptide fragments or derivatives or the salts of peptide fragments are used at a concentration of from 0.01 to 1000 ppm, the preferred use being within a range of from 0.1 to 100 ppm.

The peptide fragments used or derivatives or salts of peptide fragments are preferably diluted in one or more solvents which are permitted for cosmetic and/or pharmaceutical preparations, such as, for example, water, propylene glycol, butylene glycol, ethoxylated or propoxylated diglycol, ethanol, propanol, isopropanol glycerol, or mixtures of those solvents.

Together with the solvents, it is possible to use other additives and admixtures in the preparations according to the present invention.

Cosmetic, Pharmaceutical and/or Dermatological Preparations

The uses of the present invention may include the production of cosmetic or pharmaceutical preparations, such as, for example, shampoos, hair lotions, bath foams, bath and shower preparations, cremes, gels, lotions, alcohol or aqueous/alcohol solutions, emulsions, fatty/waxy material substances, stick type preparations, powders or ointments. Those preparations may further contain, as admixtures or additives, mild surfactants, fatty bodies, emulsifying agents, pearl-lustre waxes, consistency agents, thickening agents, super-fatty agents, stabilising agents, polymers, silicone-containing compounds, fatty substances, waxes, lecithin, phospholipids, factors for protection against UV rays, biogenic substances, antioxidants, deodorants, antiperspirants, anti-film agents, film-forming agents, expansion agents, insect repellents, self-tanning agents, tyrosine inhibitors (depigmentation agents), hydrotopes, solubilisers, preserving agents, perfume oils and dyes, or the like.

Surfactants

Anionic, non-ionic, cationic and/or amphoteric or zwitterionic surfactants may be contained as surface-active substances, and their proportion relative to the media is conventionally from 1 to 70, preferably from 5 to 50, and in particular from 10 to 30% by weight. Typical examples of anionic surfactants are soaps, alkylbenzene sulphonates, alkane sulphonates, olefin sulphonates, alkylether sulphonates, glycerin ether sulphonates, α-methylester sulphonates, sulphonated fatty acids, alkyl sulphates, alkylether sulphates, glycerin ether sulphates, fatty acid ether sulphates, mixed ether/hydroxyl sulphates, monoglycerin ether sulphates, fatty acid amide ether sulphates, mono- and dialkylsulphonates, mono- and dialkylsulphosuccinamates, sulphoglycerides, amide soaps, ether carbonic acids and the salts thereof, fatty acid isethionates, fatty acid sarcocinates, fatty acid taurides, N-acyl amino acids, such as, for example, acyl lactilate, acyl tartrate, acyl glutamate and acyl asparate, alkyloligoglucoside sulphate, protein-carrying fatty acid condensates (in particular, vegetable wheat-based products) and alkyl(ether) phosphates. If the anionic surfactants contain chains of polyglycol ether, they may have a conventional homogeneous distribution, but preferably a narrow distribution. Typical examples of non-ionic surfactants are fatty alcohol polyglycol ether, alkyl phenol polyglycol ether, fatty acid polyglycol ester, fatty acid amide polyglycol ether, fatty amino polyglycol ether, alkoxylated triglycerides, mixed ethers or mixed formals, optionally partially oxidised alkylenyl oligoglycosides or derivatives of glucoronic acid, fatty acid N-alkyl glucamides, protein hydrolysates (in particular, vegetable wheat-based products), polyol fatty acid esters, sugar esters, sorbitan esters, polysorbate esters and amino oxide esters. If non-ionic surfactants contain polyglycol ether chains, they may have conventional homogeneous distribution, but preferably a narrow distribution. Typical examples of cationic surfactants are quaternary ammonium compounds, such as, for example, aluminum chloride of dimethyldistearyl, the esterquats, in particular salts of ester of quaternised fatty acid trialkanolamine. Typical examples of amphoteric or zwitterionic surfactants are alkylbetaine, alkylamidobetaine, aminopropionate, aminoglycinate, imidazoliniumbetaine and sulphobetaine. The surfactants mentioned are exclusively known compounds. Typical examples of suitable mild surfactants, that is to say, those which are particularly well-tolerated by the skin, are fatty alcohol polyglycol ether sulphates, monoglyceride sulphates or mono- and/or dialkyl sulphosuccinates, fatty acid isethionates, fatty acid sarcocinates, fatty acid taurides, fatty acid glutamates, α-olefin sulphonates, ether carbonic acids, alkyl oligoglucosides, fatty acid glucamides, alkyl amidobetaines, protein fatty acid amphoacetals and/or condensates, the last-mentioned preferably being based on wheat protein.

Fatty Bodies

There are considered, as fatty bodies, for example, Guerbet alcohols based on a fatty alcohol having from 6 to 18, preferably 8 to 10 carbon atoms, linear $C_6$-$C_{22}$ fatty acid esters with linear or branched $C_6$-$C_{22}$ fatty alcohols or $C_6$-$C_{13}$ carbonic acid esters which are branched with linear or branched $C_6$-$C_{22}$ fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In the same manner, linear $C_6$-$C_{22}$ fatty acid esters with branched alcohols are suitable, in particular 2-ethylhexanol, $C_{18}$-$C_{38}$ alkyl hydroxycarboxylic acid ester with linear or branched $C_6$-$C_{22}$ alcohols (see document DE 19 756 377 A1), in particular dioctyl malate, linear and/or branched fatty acid esters with polyfunctional alcohols (such as, for example, propylene glycol, diol dimer or triol trimer) and/or Guerbet alcohols, triglycerides based on $C_6$-$C_{10}$ fatty acids, mixtures of mono-/di- or triglycerides based on $C_6$-$C_{18}$ fatty acids, $C_6$-$C_{22}$ fatty alcohol esters and/or Guerbet alcohols with aromatic carbonic acids, in particular benzoic acids, $C_2$-$C_{12}$ dicarbonic acid esters with linear or branched alcohols having from 1 to 22 carbon atoms or polyols having from 2 to 10 carbon atoms and from 2 to 6 hydroxyl groups, vegetable oils, branched primary alcohols, substituted cyclohexanes, linear or branched $C_6$-$C_{22}$ fatty alcohol carbonates, such as dicaprylyl carbonate (Cetiol® CC), Guerbet carbonate based on fatty alcohols having from 6 to 18, preferably 8 to 10 carbon atoms, benzoic acid esters with linear and/or branched $C_6$-$C_{22}$ alcohols (for example, Finsolv® TN), linear or branched, symmetrical or non-symmetrical dialkyl ethers having from 6 to 22 carbon atoms per alkyl group, such as, for example, dicaprylyl ether (Cétiol® OE), ring opening products of fatty acid esters which are epoxydised with polyols, silicone oil (cyclomethicone, types of silicon methicone, inter alia) and/or aliphatic or naphthenic hydrocarbons, such as, for example, squalane, squalene or dialkyl cyclohexane.

Emulsifying Agents

There are considered as emulsifying agents, for example, non-ionogenic surfactants from at least one of the following groups:

products for adding from 2 to 30 moles of ethylene oxide and/or from 0 to 5 moles of propylene oxide in linear fatty alcohol having from 8 to 22 carbon atoms, in fatty acids having from 12 to 22 carbon atoms, alkylphenols having from 8 to 15 carbon atoms in alkyl groups, such as alkylamine having from 8 to 22 carbon atoms in the alkyl residue;

alkyl and/or alkenyloligoglycoside having from 8 to 22 carbon atoms in the alkenyl/alkyl residue and ethoxylated equivalents;

products for adding from 1 to 15 moles of ethylene oxide in ricin oil and/or the hardened ricin oil;

products for adding from 15 to 60 moles of ethylene oxide in ricin oil and/or hardened ricin oil;

partial esters of glycerin and/or sorbitan with unsaturated, linear or saturated fatty acids which are branched having from 12 to 22 carbon atoms and/or hydroxycarbonic acids having from 3 to 18 carbon atoms, as well as their addition product having from 1 to 30 moles of ethylene oxide;

partial esters of polyglycerin (mean condensation degree of from 2 to 8), polyethyleneglycol (molecular weight from 400 to 5000), trimethylolpropane, pentaerythritol, sugar alcohols (for example, sorbitol), alkyl glucosides (for example, methyl glucoside, butyl glucoside, lauryl glucoside) as well as polyglucosides (for example, cellulose) with saturated and/or unsaturated fatty acids which are linear or branched having from 12 to 22 carbon atoms and/or hydroxycarbonic acids having from 3 to 18 carbon atoms, as well as their addition products having from 1 to 30 moles of ethylene oxide;

mixed esters of pentaerythritol, fatty acids, citric acid and fatty alcohol and/or mixed esters of fatty acids having from 6 to 22 carbon atoms, methyl glucose and polyols, preferably glycerin or polyglycerin;

mono-, di-, or trialkylphosphate, and mono-, di- and/or tri-PEG-alkylphosphate and the salt thereof;

wool wax alcohols;

polyxyloxane-polyalkyl-polyether copolymers or corresponding derivatives;

sequenced polymers, for example, polyethylene glycol-30 dipolyhydroxystearate;

polymer emulsifiers, such as the pemulen (TR-1, TR-2) type from Goodrich;

polyalkylene glycol's and glycerin carbonate.

Ethylene Oxide Addition Products

The ethylene oxide addition products and/or propylene oxide of fatty alcohols, fatty acid, alkyl phenol and ricin oil are known commercially available products. This is a homogeneous admixture whose intermediate alkoxylation degree corresponds to the relationship of the substance quantities of ethylene oxide and/or propylene oxide and the substrate, with which the addition reaction is introduced. $C_{12/18}$ fatty acid mono- and diesters of addition products of ethylene oxide with glycerin are agents for the introduction of fat which are known for cosmetic preparations.

Alkyl and/or Alkenyloligoglycoside

Alkyl and alkenyloligoglycoside, production thereof and use thereof are known according to the prior art. Its production is carried out in particular by conversion of glucose or oligosaccharides with primary alcohols with 8 to 18 carbon atoms. With regard to the residues of glycosides, it is considered that both monoglucosides to which a residue of cyclical sugar is bonded by means of a glycoside at the fatty alcohol and oligomeric glycosides with a degree of oligomerisation which can preferably be up to 8 are suitable. Consequently, the degree of oligomerisation is a statistical intermediate value, on which a conventional homogeneous distribution is based for those technical products.

Partial Glycerides

Typical examples of suitable partial glycerides are hydroxystearic acid monoglyceride, hydroxystearic acid diglyceride, isostearic acid monoglyceride, isostearic acid diglyceride, olefinic acid monoglyceride, olefinic acid diglyceride, ricinolic acid monoglyceride, ricinolic acid diglyceride, linolic acid monoglyceride, linolic acid diglyceride, linolenic acid monoglyceride, linolenic acid diglyceride, erucic acid monoglyceride, erucic acid diglyceride, tartric acid monoglyceride, tartric acid diglyceride, citric acid monoglyceride, citric acid diglyceride, maleic acid monoglyceride, maleic acid diglyceride as well as the technical admixtures thereof which may further contain minute quantities of subordinate triglycerides in the production process. Addition products of from 1 to 30, preferably 5 to 10 moles of ethylene oxide relative to the partial glycerins cited are also suitable.

Sorbitan Esters

There are considered, as the sorbitan ester, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitane trihydroxystearate, sorbitan monotartrate, sorbitan sesquitartrate, sorbitan ditartrate, sorbitan tritartrate, sorbitan monocitrate, sorbitan sesquicitrate, sorbitan dicitrate sorbitan tricitrate, sorbitan monomaleate, sorbitan sesquimaleate, sorbitan dimaleate, sorbitan trimaleate as well as the technical admixtures thereof. Suitable addition products also include those having from 1 to 30, preferably from 5 to 10 moles of ethylene oxide in the sorbitan ester mentioned.

Polyglycerin Esters

Typical examples of suitable polyglycerin esters are polyglyceryl-2 dipolyhydroxystearate (Dehymuls® PGPH), polyglycerin-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cethyl ether (Chimexane® NL), polyglyceryl-3 distearate (Cremophor® GS 32) and polyglyceryl polyricinoleate (Admul® WOL 1403), polyglyceryl dimerate isostearate, as well as admixtures thereof. Examples of polyol ester which are also suitable are the mono-, di- and triesters of trimethylolpropane or pentaerythritol which is optionally converted having from 1 to 30 moles of ethylene oxide with lauric acid, fatty coconut acid, fatty tallow acid, palm acid, stearic acid, oleic acid, behenic acid and the like.

Anionic Emulsifying Agents

Typical anionic emulsifying agents are fatty aliphatic acids having from 12 to 22 carbon atoms, such as, for example, palm acid, stearic acid, behenic acid as well as dicarbonic acids having from 12 to 22 carbon atoms, such as, for example, azelaic acid or sebacic acid.

Amphoteric and Cationic Emulsifying Agents

Furthermore, zwitterionic surfactants can be used as emulsifying agents. As zwitterionic surfactants of such surface active compounds are specific, which carry in the molecule at least a quaternary ammonium group and at least one carboxylate and/or sulphonate group. Particularly suitable zwitterionic surfactants are the betaines, such as N-alkyl-N,N-dimethylammonium glycinate, for example, coco alkyldimethylammonium glycinate, N-acylamino-propyl-N, N-dimethylammonium glycinate, for example, coco acylaminopropyldimethylammonium glycinate, and 2-alkyl-3-carboxylmethyl-3-hydroxyethylimidazoline with, in each case, from 8 to 18 carbon atoms in the acyl or alkyl group, as well as coco acylaminoethylhydroxyethyl-carboxymethylglycinate. The fatty acid amide derivative known under the designation CTFA Cocamidopropyl Betaine is particularly preferred. Emulsifying agents which are also suitable are ampholyte surfactants. Ampholyte surfactants are intended to refer to those surface active compounds which further contain a $C_8$-$C_{18}$ alkyl group and/or $C_8$-$C_{18}$ acyl group in the molecule, at least one free amino group and at least one —COOH— or —$SO_3H$— group and which are capable of forming internal salts. Examples of ampholyte surfactants which are suitable are N-alkylglycine, N-alkylpropionic acids, N-alkylaminobutyric acids, N-alkyliminopropionic acids, N-hydroxyethyl-N-alkylamidopropylglycines, N-alkyltaurides, N-alkylsarcosines, 2-alkylaminopropionic acids, alkylaminoacetic acids with, in each case, from 8 to 18 carbon atoms in the alkyl group. Particularly preferred ampholyte surfactants are coco N-alkylaminopropionate, coco acylaminoethylaminopropionate and $C_{12}$/$C_{18}$ acyl sarcosine. Finally, there are also considered, as emulsifying agents, cationic surfactants, those of the type of the esterquats, preferably fatty diacid triethanolaminester salts, and preferably those which are methyl quaternised are particularly preferred.

Fatty Substances and Waxes

Typical examples of a fatty substance are glycerides, that is to say, animal or vegetable products which are liquid or solid and which principally comprise glycerin ester mixed with higher fatty acids; there are considered, as waxes, inter alia, natural waxes, such as Candelilla wax, Carnauba wax, Japan wax, Alfa wax, liege fibre wax, guaruma wax, wheat germ oil wax, sugar cane wax, Ouricury wax, Montana wax, beeswax, shellac wax, spermaceti, lanolin (wool wax), croupion fats, ceresin, ozokerite (wax of Moldova), petrolatum, paraffin waxes, microwaxes; chemically modified waxes (dry waxes), such as, for example, Montana ester waxes, Sasol waxes, hydrogenated jojoba waxes as well as synthetic waxes, such as, for example, polyalkylene waxes and polyethyleneglycol waxes. Together with the fatty substances, there are also considered, as additives, substances which are similar to the fats, such as lecithins, and phospholipids. The person skilled in the art understands, by the designation lecithins, the glycerin-phospholipids which are formed from fatty acids, glycerin, phosphoric acid and choline by esterification. Lecithins are most often known to the person skilled in the art as phosphatidylcholines (PC). Examples of natural lecithins include cephalins which are characterised as phosphatidic acids and derivatives of 1,2-diacyl-sn-glycerin-3-phosphoric acids. At the same time, phospholipids are intended to refer to conventional monoesters and, preferably, phosphoric acid diesters with glycerin (glycerin phosphate) which are generally considered to be fatty substances. At the same time, there are also considered sphingosines or sphingolipids.

Pearl Gloss Waxes

There are considered, as pearl gloss waxes, for example: glycol alkylene ester, in particular glycol ethylene distearate, fatty acid alkanolamide, in particular coco fatty acid diethanolamide; partial glycerins, in particular stearic acid monoglycerides; plurifunctional carbonic acid esters and/or which are optionally substituted by a hydroxy having fatty alcohols having from 6 to 22 carbon atoms, in particular long-chain tartaric acid esters, fatty substances, such as, for example, fatty alcohols, fatty ketones, fatty aldehydes, fatty ethers and fatty carbonates, which have a total of at least 24 carbon atoms, in particular lauric and distearylic ether; fatty acids, such as stearic acid, hydroxystearic acid or behenic acid, ring opening products of the olefin expoxides, having from 12 to 22 carbon atoms, with fatty alcohols having from 12 to 22 carbon atoms and/or polyols having from 2 to 15 carbon atoms and from 2 to 10 hydroxyl groups, as well as mixtures thereof.

Consistency Agents and Thickening Agents

There are considered, as consistency agents, firstly, fatty alcohols or fatty hydroxy alcohols having from 12 to 22 carbon atoms and preferably from 16 to 18 carbon atoms and, in the same manner, partial glycerins, fatty acids or fatty hydroxy acids. A combination of those substances with oligoalkylglucosides and/or fatty acid N-methylglucamides having equivalent chain lengths and/or polyglycerolpoly-12-hydroxystearates is preferred. Suitable thickening agents are, for example, those of the Aérosil type (hydrophilic silicic acids), polysaccharides, in particular xanthane gum, guarguar, agar-agar, alginates, tyloses, carboxymethylcellulose and hydroxyethyl- or hydroxypropylcellulose, and furthermore diesters and monoesters of polyethylene glycol having a high molecular weight of fatty acid, polyacrylates (for example, of the Carbopole® and Permulen type from Goodrich; of Synthalene® of Sigma; of the keltrol, of kelco types; of the Sepigel of Seppic types; of the Salcare type from Allied Colloids), polyacrylamides, polymers, polyvinyl alcohols and polyvinylpyrrolidone. Bentonite is also presented as being particularly effective, such as Bentone® Gel VS-5PC (Rheox), in the case of which it is a mixture of cyclopentasiloxane and disteardimonium hectorite and propylene carbonate. Other surfactants are also considered, such as, for example, ethoxylated fatty acid glycerides, fatty acid esters of polyols, such as, for example, pentaerythritol or trimethylolpropane, fatty alcohol ethoxylates having a narrow homogeneous distribution, or alkyloligoglucosides, as well as electrolytes, sodium chloride electrolytes and ammonium chloride electrolytes.

Super-Fatty Agents

It is possible to use, as super-fatty solutions, substances such as, for example, lanoline and lecithin, as well as derivatives of lecithin and lanoline which are acylated or polyethoxylated, fatty acid esters of polyol, monoglycerides and alcanolamides of fatty acids, the last-mentioned at the same time being used as foaming stabilisers.

Stabilizers

It is possible to use, as stabilizers, metal salts of fatty acids, as well as magnesium stearate, aluminum stearate and/or zinc stearate, as well as ricin oleate.

Polymers

Suitable cationic polymers are, for example, cationic cellulose derivatives, such as, for example a quaternary hydroxyethylcellulose which is obtained under the reference polymer JR 400® from Amerchol, cationic starches, copolymers of diallylic ammonium salts and acrylamides, quaternary polymers of vinylpyrrolidone/vinylimidazole, such as, for example, Luviquat® (BASF), condensation products of polyglycols and amines, polypeptides of quaternised collagen, such as, for example, hydrolysed collagen of lauryldimonium hydroxypropyl (Lamequat® L/Grünau), polypeptides of quaternised wheat, polyethyleneimine, cationic silicone polymers, such as, for example, amidomethicones, copolymers of adipic acid and dimethylaminohydroxypropyldiethylenetriamine (Cartaretine®/Sandoz), acrylic acid copolymers having dimethyldiallylammonium chloride (Merquat® 550/Chemviron), polyaminopolyamides, such as, for example, those described in document FR 2252840 A, as well as their water-soluble cross-linked polymers, their derivatives from cationic chitin, such as, for example, quaternised chitosans, optionally distributed in a microcrystalline manner, condensation products of dihalogenoalkyls, such as, for example, dibromobutane comprising bisdialkylamines, such as, for example, bisdimethylamino-1,3-propane, cationic guar gum, such as, for example, Jaguar® CBS, Jaguar® C-17, Jaguar® C-16 from the company Celanese, polymers of quaternised ammonium salt, such as, for example, Mirapol® A-15, le Mirapol® AD-1, Mirapol® AZ-1 from the company Miranol.

Anionic, zwitterionic, amphoteric and non-ionic polymers may be considered, such as, for example, copolymers of vinyl acetate/crotonic acid, copolymers of vinylpyrrolidone/vinyl acrylate, copolymers of vinyl acetate/butyl maleate/isobornyl acrylate, copolymers of methylvinyl ether/maleic acid anhydride and their esters, polyacrylic acids cross-linked with polyols, and non-cross-linked, copolymers of acrylamidopropyltrimethylammonium chloride/acrylate, copolymers of octylacrylamide/methyl methacrylate/tert.butylaminoethyl methacrylate/2-hydroxypropyl methacrylate, polyvinylpyrrolidone, copolymers of vinylpyrrolidone/vinyl acetate, terpolymers of vinylpyrrolidone/dimethylaminoethyl methacrylate/vinyl caprolactam, as well as, optionally, derived cellulose esters and silicones.

Silicone-Containing Compounds

Suitable silicone-containing compounds are, for example, dimethylpolysiloxanes, methylphenylpolysiloxanes, cyclical silicones as well as compounds based on silicone which are amino modified, fatty acid modified, alcohol modified, polyether modified, epoxy modified, fluoro modified, glycoside modified and/or alkyl modified, which may be, at ambient temperature, both in liquid form and in the form of resins. Furthermore, simethicones are suitable, in the case of which they are mixtures of dimethicones with an intermediate chain length of from 200 to 300 units of dimethylsiloxane and hydrogenated silicates.

Protective Filter Against UV Rays

UV protection factors are intended to refer to, for example, organic substances which are present at ambient temperature in crystalline or liquid form and which are capable of absorbing ultraviolet radiation and which return the energy stored in the form of very long wave radiation, for example, heat. UV-B filters may be soluble in oil or water. Substances which are soluble in oil may, for example, include the following:

3-benzylidene camphor or 3-benzylidene norcamphor and the derivatives thereof, for example, 3-(4-methylbenzylidene) camphor;

derivatives of 4-aminobenzoic acid, preferably 2-ethylhexyl ester of 4-(dimethylamino)benzoic acid, 2-octyl ester of 4-(dimethylamino)benzoic acid and the amyl ester of 4-(dimethylamino)benzoic acid;

esters of cinnamic acid, preferably 2-ethylhexyl ester of 4-methoxycinnamic acid, the propyl ester of 4-methoxycinnamic acid, the isoamyl ester of 4-methoxycinnamic acid, the 2-ethylhexyl ester of 2-cyano-3,3-phenylcinnamic (octocrylene) acid;

esters of salicylic acid, preferably the 2-ethylhexyl ester of salicylic acid, the 4-isopropylbenzyl ester of salicylic acid, the monomethyl ester of salicylic acid;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 2-ethylhexyl esters of 4-methoxybenzomalonic acid;

derivatives of triazine, such as, for example, 2,4,6-trianilino-(p-carbo-2'-ethyl-1'-hexyloxy)-1,3,5-triazine and octyl triazone or dioctyl butamido triazone (Uvasorb® HEB);

propane-1,3-diones, such as, for example, 1-(4-tert.butylphenyl)-3-(4'methoxyphenyl)propane-1,3-dione;

derivatives of ketotricyclo(5.2.1.0)decane.

Substances which are soluble in water and which may be considered include:

2-phenylbenzimidazol-5-sulphonic acid and the alkaline, alkaline-earth, ammonium, alkylammonium, alcanolammonium and glucammonium salts thereof;

sulphonic acid derivatives of benzophenones, preferably 2-hydroxy-4-methoxybenzophenone-5-sulphonic acids and the salts thereof;

sulphonic acid derivatives of 3-benzylidene camphor, such as, for example, 4-(2-oxo-3-bornylidenemethyl)benzenesulphonic acids and 2-methyl-5-(2-oxo-3-bornylidene)sulphonic acids and the salts thereof.

Typical UVA filters may include in particular derivatives of benzoylmethanes, such as, for example, 1-(4'-tert.butylphenyl)-3-(4'-methoxyphenyl)propane-1,3-dione, 4-tert.-butyl-4'-methoxydibenzoylmethane (Parsol® 1789), 1-phenyl-3-(4'-isopropylphenyl)propane-1,3-dione as well as the enamine compounds thereof. UVA and UVB filters may naturally be used as a mixture. Particularly advantageous combinations comprise derivatives of benzoylmethane, such as, for example, 4-tert.-butyl-4'-methoxydibenzoylmethane (Parsol® 1789) and 2-ethylhexyl ester of 2-cyano-3,3-phenylcynnamic (octocrylene) acid in combination with an ester of cinnamic acid, preferably 2-ethylhexyl ester of 4-methoxycinnamic acid and/or the propyl ester of 4-methoxycynnamic acid and/or the isoamyl ester of 4-methoxycynnamic acid. Combinations of that type are particularly advantageous when combined with filters which are soluble in water, such as, for example, 2-phenylbenzimidazol-5-sulphonic acid, and the alkaline, alkaline-earth, ammonium, alkylammonium, alkanolammonium and glucammonium salts thereof.

Together with the soluble substances mentioned, there may also be considered, for this purpose, non-soluble pigments, that is to say, oxides or salts of metals which are finely dispersed. Suitable metal oxides may include in particular, for example, titanium dioxide, zinc oxide, as well as iron oxide, zirconium, silicon, manganese, aluminum, cerium oxides as well as mixtures thereof. There are used, as the salts, silicate (talc), barium sulphate and zinc stearate. The oxides and salts are used in the form of pigments for emulsions which protect and care for the skin and for decorative cosmetics. The particles must consequently have an intermediate diameter of less than 100 nm, preferably from 5 to 50 nm and in particular from 15 to 30 nm. They may have a spherical shape and they may also be used as particles which have a shape which is ellipsoid or which diverges from the spherical shape in different manners. The pigments may also act superficially, that is to say, be in hydrophilic or hydrophobic form. Typical examples are coated titanium dioxides, such as, for example, titanium dioxide T 805 (Degussa) or Eusolex® T2000 (Merck). There may be considered, as hydrophobic coating agents, above all silicones and, in particular, trialkoxyoctylsilanes or simethicones. Use is preferably made, as agents for protection against the effects of the sun, of the nano- or micropigments. Micronised zinc oxide is preferably used.

Biogenic and Antioxidant Substances

Biogenic substances should be understood to refer to, for example, tocopherol, tocopherol acetate, tocopherol palmitate, ascorbic acid, (deoxy)ribonucleic acid and the fragmentation products thereof, β-glucans, retinol, bisabol, allantoine, phytantriol, panthenol, AHA acids, amino acids, ceramides, pseudoceramides, essential oils, plant extracts, as well as, for example, prunus extract, bambaranus extract and vitamin-containing complexes.

The antioxidants interrupt the photochemical reaction chain which starts when UV radiation penetrates the skin. Typical examples thereof are amino acids (for example, glycine, histidine, tyrosine, tryptophan) and the derivatives thereof, imidazoles (for example, urocanic acid) and the derivatives thereof, peptides, such as D,L-carnosine, D-carnosine, L-carnosine and the derivatives thereof (for example, anserine), carotinoid, carotine (for example, α-carotine, β-carotine, lycopine) and the derivatives thereof, chlorogenic acids and the derivatives thereof, lipoic acids and the derivatives thereof (for example, dihydrolipoic acid), aurothioglucose, propylthiouracil and other thiols, (for example, thioredoxine, glutathione, cysteine, cystine, cystamine and the glycosyl, N-acetyl, methyl, ethyl, propyl, amyl, butyl and lauryl esters thereof, palmitoyl, oleyl, γ-linoleyl, cholesteryl and glycerol esters thereof) as well as the salts thereof. Thiodipropionic acid, dilaurylthiodipropionate, distearylthiodipropionate and the derivatives thereof, esters, ethers, peptides, lipides, nucleotides, nucleosides and salts) as well as sulphoximine compounds (for example, buthioninesulphoximine, homocysteinesulphoximine, buthioninesulphide, penta-, hexa-, heptathioninesulphoximine) in compatible doses (for example, pmol up to μmol/kg). Other metal chelating agents (for example, α-hydroxy fatty acids, palmitic acid, phytic acid, lactoferine), α-hydroxy acids (for example, citric acid, lactic acid, maleic acid), huminic acid, gallic acid, gallic extracts, bilirubine, biliverdine, EDTA, EGTA and the derivatives thereof, unsaturated fatty acids and the derivatives thereof (far example, γ-linolenic acid, linolic acid, oleic acid), folic acid and the derivatives thereof, ubiquinone and ubiquinol and the derivatives thereof, vitamin C and the derivatives thereof (for example, ascorbilic palmitate, Mg-ascorbilic phosphate, ascorbilic acetate), tocopherols and the derivatives thereof (for example, vitamin E-acetate), vitamin A and the derivatives thereof, (vitamin A-palmitate) as well as coniferyl benzoate of benzoic resin, rutinic acid and the derivatives thereof, α-glycosylrutin, ferulic acid, furfurylidene glucitol, carnosine, butylhydroxytoluene, butylhydroxyanisol, nordihydro guajak resin acid, nordihydro guajaret acid, trihydroxybutyrophenone, uric acid and the derivatives thereof, mannose and the derivatives thereof, superoxide-dismutase, zinc and the derivatives thereof (for example, ZnO, ZnSO$_4$), selenite and its derivatives (for example, seleno-methionine), stilbene and its derivatives (for example, stilbenoxide, trans-stilbene oxide) and suitable derivatives according to the present invention (salts, esters, ethers, sugar, nucleotides, nucleosides, peptides and lipids) of those active substances mentioned.

Deodorants and Substances Inhibiting Germs

Cosmetic deodorants (deodorising agents) act against body odors, conceal them or eliminate them. Body odors result from the influence of bacteria present on the skin on apocrine perspiration, and decomposition products having the unpleasant odor are formed. Some deodorants consequently contain active ingredients which act as agents inhibiting germs, enzyme inhibitors, agents which absorb odors or which conceal them.

Agents Inhibiting Germs

All substances which are effective against Gram-positive bacteria are particularly suitable as agents for inhibiting germs, for example, 4-hydroxybenzoic acid and the salts thereof and esters, N-(4-chlorophenyl)-N'-(3,4-dichlorophenyl)urea, 2,4,4'-trichloro-2'-hydroxydiphenyl(triclosane) ether, 4-chloro-3,5-dimethylphenol, 2,2-methylene-bis(6-brom-4-chlorophenol), 3-methyl-4-(1-methylethyl)phenol, 2-benzyl-4-chlorophenol, 3-(4-chlorophenoxy)-1,2-propanediol, 3-iodo-2-propinylbutylcarbamate, chlorohexidine, 3,4,4'-trichlorocarbanilide (TTC), antibacterial olfactory substances, thymol, thymine oil, eugenol, clove oil, methanol, mint oil, farnesol, phenoxyethanol, glycerol monocaprinate, glycerol monocaprylate, glycerol monolaurate (GML), diglycerol monocaprinate (DMC), salicylic acid-N-alkylamide, such as, for example, salicylic acid n-octylamide or salicylic acid n-decylamide.

Enzyme Inhibitors

Esterase inhibitors are particularly suitable as enzyme inhibitors. In this case, these are preferably trialkyl citrates, for example, trimethyl citrate, tripropyl citrate, triisopropyl citrate, tributyl citrate and, in particular, triethyl citrate (Hydagen® CAT). The substances inhibit enzymatic activity and consequently reduce the formation of odors. Other substances which may be considered as esterase inhibitors are sterol sulphate or sterol phosphate, such as, for example, the sulphate or phosphate of lanosterine, chlosterine, campesterine, stigmasterine, sistosterine, dicarbonic acids and the ester thereof, such as, for example, glutaric acid, the monoethyl ester of glutaric acid, the diethyl ester of glutaric acid, adipic acid, the monoethyl ester of adipic acid, the diethyl ester of adipic acid, malonic acid and the diethyl ester of malonic acid, hydroxycarbonic acid and the esters thereof, as well as, for example, citric acid, maleic acid, tartric acid or the diethyl ester of tartric acid as well as zinc glycinate.

Odor Absorbing Agents

Substances suitable for acting as odor absorbing agents are those which admit compounds which form odors and which can further be fixed. They reduce the partial pressure of the various components and also consequently reduce their propagation rate. It is consequently important for the perfumes to remain unchanged. The agents which absorb the odors do not have any antibacterial effectiveness. They contain, for example, as the principal component, a complex zinc salt of ricinoleic acid and, in particular neutral olfactory substances which are known to the person skilled in the art as fixing agents, such as, for example, labdanum extracts, for example, or styrax extracts or specific derivatives of abietic acid. Olfactory substances or perfume oils are used as products which mask odors and which confer on the deodorants, in addition to their function as products which mask the odors, a scent. Perfume oils may include, for example, mixtures of natural and synthetic olfactory substances. Natural olfactory substances are extracts from plants, stalks and leaves, fruits, fruit rind, roots, wood, herbs and aromatic plants, needles, branches as well as resins and natural balsams. It is also possible to use raw materials of animal origin, such as, for example, civet and beaver. Typical synthetic olfactory compounds are products of the ester, ether, aldehyde, ketone, alcohol and hydrocarbon type. Compounds of olfactory substances of the ester type are, for example, benzyl acetate, p-tert.-butylcyclohexyl acetate, linalyl acetate, phenylethyl acetate, linalyl benzoate, benzyl formiate, allylcyclohexyl propionate, styrallyl proprionate and benzyl salicylate. The ethers include, for example, benzylethyl ether, and aldehydes include, for example, linear alcanales having from 8 to 18 carbon atoms, citral, citronellal, citronellyloxyacetalaldehyde, cyclamen aldehyde, hydroxycitronellal, lilial and bourgeonal; the ketones include ionones and methylcedrylketone, the alcohols include anethol, citronellol, eugenol, isoeugenol, geraniol, linalool, phenylethyl alcohol and terpineol; the hydrocarbons include principally the terpenes and natural balsams. Preferably, however, mixtures of various olfactory substances are used and together produce a vivid scent. Essential oils which have relatively low volatility and which are mostly used as aromatic compounds are also suitable as perfume oils, for example, sage oil, camomile oil, clove oil, balm oil, mint oil, cinnamon leaf oil, lime blossom oil, juniper berry oil, vetiver oil, oliban oil, galbanum oil, labolanum oil and lavender oil. There are preferably used bergamot oil, dihydromyrcenol, lilial, lyral, citronellol, phenylethyl alcohol, α-hexylcinnamic aldehyde, geraniol, benzyl acetone, cyclamen aldehyde, linalool, boisambrene-forte, ambroxane, indol, hedione, sandelice, lemon oil, mandarin oil, orange oil, allylamyl glycolate, clovertal, lavender oil, muscat, sage oil, β-damascone, geranium bourbon oil, cyclohexyl salicylate, vertofix coeur, iso-E-super, fixolide NP, evernyle, gamma iraldeine, phenylacetic acid, geranyl acetate, benzyl acetate, rose oxide, romilliat, irotyl and floramate, alone or in mixture.

Anti-Perspirants

Anti-perspirants or deodorants reduce, by influencing the activity of the ecrine sudoriparous glands, the formation of sweat and also act against dampness of the armpits and body odors. Aqueous or anhydrous formulations for anti-perspirants generally contain the following substances:

astringent substances,
fatty components,
non-ionic emulsifying agents,
coemulsifying agents,
consistency agents,
additives, such as thickening agents or complexing agents and/or
non-aqueous solvents such as, for example, ethanol, propylene glycol and/or glycerol.

Above all, aluminum, zirconium or zinc salts are suitable as astringent anti-perspiration substances. Suitable antihydrotic active ingredients of this type are, for example, aluminum chloride, aluminum chlorohydrate, aluminumdichlorohydrate, aluminum sesquichlorohydrate and the complex compounds thereof, for example, with 1,2 propyleneglycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, for example, with amino acids, such as glycerol. At the same time, conventional water-soluble or oil-soluble additives may be present in anti-perspirants in low quantities. Those oil-soluble additives may be, for example:

essential oils which smell pleasant, protect the skin or are anti-inflammatory,
synthetic active ingredients which protect the skin and/or oil-soluble perfume oils.

Conventional water-soluble additives are, for example, preservatives, water-soluble olfactory substances, agents for regulating the pH value, for example, buffer mixtures, water-soluble thickening agents, for example, soluble synthetic or natural polymers, for example, xanthan gum, hydroxyethyl-cellulose, polyvinyl pyrrolidone or high molecular weight polyethylene oxide.

Film-Forming Agents

Conventional film-forming agents are quitosane, microcrystalline quitosane, quaternised quitosane, polyvinyl pyrrolidone, copolymerisates of vinyl pyrrolidone/vinyl acetate, polymers from the series of acrylic acids, quaternary cellulose derivatives, collagen, hyaluric acid, or the salts thereof and similar compounds.

Anti-Pellicular Substances

Anti-pellicular substances may include piroctone olamine (salt of 1-hydroxy-4-methyl-6-(2,4,4-trimethylpentyl)-2-(1H)-pyridinonmonoethanolamine), Baypival® (Climbazole), Ketoconazol®, (4-acetyl-1-{-4-[2-(2,4-dichlorophenyl)r-2-(1H-imidazol-1-ylmethyl)-1,3-dioxylan-c-4-ylmethoxyphenyl}piperazine, Ketoconazol, Elubiol, selenium disulphite colloidal sulphur, monooleate of sulphurous polyethylene glycol sorbitane, ricinolic sulphur polyethoxylate, goufron/sulphur distillates, salicylic acid (or in conjunction with hexachlorophene), the sodium salt of sulphosuccinate monoethanolamide of undexylene acid, Lamepon® UD (a condensate of undexylene acid protein), zinc pyrithione, aluminum pyrithione and magnesium pyrithione/magnesium dipyrithione sulphate.

Expansion Agents

It is possible to use, as expansion agents for the aqueous phase, montmorillonite, mineral substances of pemulen clay, as well as types of carbopol modified by the alkyl (Goodrich). Other suitable polymers or expansion agents may be taken from a reading of R. Lochhead in Cosm. Toil. 108, 95 (1993).

Insect Repelling Agents

It is possible to consider, as an insect repellent, N,N-diethyl-m-toluamide, 1,2-pentanediol and ethyl butylacetylaminopropionate.

Self-Tanning Agents and Depigmentation Agents

Dihydroxyacetone is suitable as a self-tanning agent. Inhibitors of tyrosine which prevent the formation of melanin and which are used in depigmentation solutions may include arbutin, ferulic acid, kojic acid, coumarin acid and ascorbic acid (vitamin C).

Hydrotropes

In order to improve fluidity behaviour, there may be used, inter alia, hydrotropes, such as, for example, ethanol, isopropyl alcohol and polyols. The polyols which are considered in this case preferably have from 2 to 15 carbon atoms and at least 2 hydroxy groups. The polyols may further contain other functional groups, in particular amino groups, or can be modified with nitrogen. Typical examples are:
  glycerol;
  alkylene glycol, such as, for example, ethylene glycol, diethylene glycol, propylene glycol, butylene glycol, hexylene glycol as well as polyethylene glycol having a mean molecular weight of from 100 to 1,000 daltons;
  technical mixtures of oligoglycerol with a condensation degree of from 1.5 to 10 such as, for example, technical mixtures of diglycerol having a content of diglycerol of from 40 to 50% by weight;
  compounds of methylol, such as, for example, trimethylolethane, trimethylolpropane, trimethylolbutane, pentaerythritol and dipentaerythritol;
  weak alkylglucosides, in particular those having from 1 to 8 carbon atoms in the alkyl residue, such as, for example, butylglucoside and methylglucoside;
  sugar alcohols having from 5 to 12 carbon atoms, such as, for example, sorbitol or manitol,
  sugar having from 5 to 12 carbon atoms, such as, for example, glucose or saccharose;
  amino sugars, such as glucamine;
  dialcohol amines, such as diethanol amine or 2-amino-1,3-propanediol.

Preservative Agents

Suitable preservative agents include, for example, phenoxyethanol, a solution of formaldehyde, paraben, pentanediol and sorbic acid, as well as silver complexes which are known under the commercial reference Surfacine® and other classes of substances set out in annex 6, parts A and B of the cosmetic regulations.

Perfume and Aromatic Oils

Perfume oils include mixtures of synthetic and natural olfactory substances. Natural olfactory substances are extracts from plants (lily, lavender, rose, jasmine, neroli, Ylang-Ylang), stems and leaves (geranium, patchouli, petit grain), fruits (anise, coriander, cumin, juniper), fruit peel (bergamot, lemon, orange), roots (nutmeg, angelica, celery, cardamom, costus, iris, calmus), woods (pinewood, sandalwood, guaiac wood, cedar wood, rose wood), herbs and aromatic plants (tarragon, lemon grass, sage, thyme), needles and branches (spruce, fir, pine, dwarf mountain pine), resins and natural balsams (galbanum, elemi, benzoin, myrrh, olibanum, opoponax). Raw animal substances may also be considered such as, for example, civet and beaver. Typical synthetic olfactory compounds are products of the ester, ether, aldehyde, ketone, alcohol and hydrocarbon type. Olfactory substances of the ester type are, for example, benzyl acetate, phenoxyethyl isobutyrate, p-tert.-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. Ethers include, for example, benzylethyl ether, and aldehydes include, for example, linear alcanales having from 8 to 18 carbon atoms, citral, citronellal, citronellyloxyacetalaldehyde, cyclamen aldehyde, hydroxycitronellal, lilial and bourgeonal; the ketones include ionones, α-isomethylionone, and methylcedrylketone, the alcohols include anethol, citronellol, eugenol, isoeugenol, geraniol, linalool, phenylethyl alcohol and terpineol; the hydrocarbons principally include the terpenes and natural balsams. Preferably, however, mixtures of various olfactory substances are used, which together produce a vivid perfume. Essential oils which have low volatility and which are mainly used as aromatic components are also suitable as perfume oils, for example, sage oil, camomile oil, clove oil, melisse oil, mint oil, canella leaf oil, lime blossom oil, juniper berry oil, vetiver oil, oliban oil, galbanum oil, labolanum oil and lavender oil. Use is preferably made of bergamot oil, dihydromyrcenol, lilial, lyral, citronellol, phenylethyl alcohol, α-hexylsuccinnamic aldehyde, geraniol, benzyl acetone, cyclamen aldehyde, linalool, boisambrene-forte, ambroxan, indol, hedione, sandelice, lemon oil, mandarin oil, orange oil, allylamyl glycolate, cyclovertal, lavender oil, muscat, sage oil, β-damascone, geranium oil bourbon, cyclohexyl salicylate, vertofix coeur, iso-E-super, fixolide NP, evernyle, iraldeine gamma, phenylacetic acid, geranyl acetate, benzyl acetate, rose oxide, romillate, irotyl and floramate, alone or in admixture.

Perfumes include, for example, peppermint oil, spearmint oil, aniseed oil, star aniseed oil, caraway oil, eucalyptus oil, fennel oil, lemon oil, wintergreen oil, clove oil, menthol and the like.

Dyes

Dyes which can be used include the substances permitted and suitable for cosmetic purposes, such as, for example, those listed in the publication <<Kosmetische Färbemittel>> der Farbstoffkommission der Deutschen Forschungsgemeinschaft, Edition Chemie, Weinheim, 1984, p. 81-106. Examples include cochineal red A (C.I. 16255), patented blue V (C.I. 42051), indigotine (C.I. 73015), chlorophylline (C.I. 75810), yellow quinoline (C.I. 47005), titanium dioxide (C.I. 77891), indanthrene blue RS (C.I. 69800) and garance lacquer (C.I. 58000). It is also possible to use luminol as a luminescent dye. These dyes are conventionally used in concentrations of from 0.001 to 0.1% by weight relative to the total admixture.

The total proportion of additives and admixtures can be from 1 to 50, preferably from 5 to 40% by weight, relative to the agent. The production of the agent may be carried out by processes in the cold or hot state, and preferably work is carried out in accordance with a phase inversion temperature process.

Another object of the present invention relates to cosmetic preparations containing a peptide fragment derivative of parathyroid hormone which complies with the structure

R1-NH-AA-R2 where R1 is selected from the group which is formed by —H, by a linear saturated or unsaturated acyl group or branched saturated or unsaturated acyl group having from 1 to 24 carbon atoms, which can be functionalized with an —OH, —SH, —COOH or —CONH2 group, or a sterol group which is bonded by a functional group, such as a diacid with the peptide;

where R2═—OH, or the OH group is functionalized by a linear saturated or unsaturated alkyl group or a branched saturated or unsaturated alkyl group having from 1 to 24 carbon atoms or a sterol group;

where AA corresponds completely or partially to the amino acid sequence according to SEQ. ID NO: 1 of PTH (28-34) corresponding to the PTH (28-34) region (Leu-Gln-Asp-Val-His-Asn-Phe);

with the provision that R1 then corresponds to H only when R2 is different from —OH, or R1 is different from H when R2 corresponds to OH.

The residue R1 is preferably selected from the group which is formed by the acetyl group, by the ethanoyl group, by the propionyl group, by the butanoyl group, by the decanoyl group, by the palmitoyl group, by the stearoyl group, by the oleyl group, by the lipoyl group, by the linoleyl group and by the conjugated linoleyl group. The acetoyl group is particularly preferred of these groups.

The preferred sterol group represents cholesterol, stigmasterol, sitosterol, brassicasterol or sphingolipid, which group is bonded by a functional group, such as a diacid, for example, a succinic acid.

When R2 represents a sterol group, it is preferably selected from the group which is formed by cholesterol, stigmasterol, sitosterol, brassicasterol or sphingolipid.

The amino acid sequence AA, which corresponds completely or partially to the amino acid sequence according to SEQ ID No 1, corresponding to the region of PTH (28-34) is preferably position 2 to 5 of SEQ ID No 1 corresponding to the region of PTH (29 to 32) (Gln-Asp-Val-His) or preferably comprises pGlu-Asp-Val-His.

EXAMPLES

Example 1

Effects on the Growth of Human Dermis Fibroblasts

The object of this test is to examine the regenerating and revitalising activities of cultures of human dermis fibroblasts in vitro.

Human dermis fibroblasts were incubated in a standard medium for cell cultures with foetal calf serum (FCS). After culture for one day at 37° C. and with a 5% content of $CO_2$, the medium was changed for a standard medium with different concentrations of peptides. After further incubation for three days and six days, the number of living cells was established by establishing the DNA cell content with a fluorescent probe (Hoechst 33258).

The results are set out in Table 1 in the form of a mean value based on the four tests in triplicate in % relative to a control medium, whose standard medium did not contain any additive.

TABLE 1

| Peptide | Concentration in % | DNA after culture for 3 days | DNA after culture for 6 days |
| --- | --- | --- | --- |
| Control | | 100 | 100 |
| Gln-Asp-Val-His | 0.001 | 162 | 119 |
| | 0.003 | 155 | 115 |

The PTH fragment (29-32) corresponding to position 2 to 5 of SEQ ID NO: 1 (Gln-Asp-Val-His) stimulates the growth of human dermis fibroblasts cultivated from biopsies of healthy adult subjects. The activity is still detectable after 6 days, even without any change in the cell culture medium.

Example 2

Effect on Human Dermal Fibroblast mRNA Profiles

The aim of this study is to detect the variation of mRNA profile of human dermal fibroblast induced by treatment with the PTH(29-32) peptide fragment.

Normal human dermal fibroblast were cultured in standard medium supplemented with foetal calf serum (FCS) during three days in a 5% $CO_2$ atmosphere. After cultures, the medium was changed by a standard medium either supplemented with PTH(29-32) peptide fragment at 5 μg/ml or not. After an incubation of either 3 or 24 hours, cultures were arrested and total RNAs of the different cultures were extracted. The cDNAs obtained from peptide-treated RNAs or from non-treated RNAs were labelled with cyanine-3 and cyanine-5, respectively.

Mixture of treated and non-treated cDNAs were hybridised on commercially Panhuman® 10K (MW Biotech, Roissy Charles-de-Gaulle, France) cDNA-array allowing to study near to 10,000 gene expressions. After highly stringent washing, cyanine-3 and cyanine-5 fluorescences were measured, allowing to evaluate a non-treated versus treated expression ratio of each analyzed gene.

Table 2 displays analysis of relevant genes from two independent assays. Results are expressed as $Log_2$ of the ratio between the measured expression of genes in the treated vs non-treated conditions.

TABLE 2

Analysis of gene expression on cDNA-array

| family | gene | description name | Analysis after 3 h incubation | | Analysis after 24 h incubation | |
|---|---|---|---|---|---|---|
| | | | Log2 (treated/ non-treated) | Expression evolution | Log2 (treated/non-treated) | Expression evolution |
| TGF signal | tgfbr3 | transforming growth factor, beta receptor III (betaglycan,); | 2.00 | increase | 1.54 | increase |
| Growth factor | ctgf | connective tissue growth factor | 0.77 | increase | 0.74 | increase |
| Growth factor | fgf2 | fibroblast growth factor 2; | 0.86 | increase | ND | ND |
| Extra-cellular matrix | col1a1 | alpha 1 type i collagen | 0.93 | increase | ND | ND |
| Extra-cellular matrix | itgb5 | integrin, beta 5 | 0.05 | no variation | 0.68 | increase |
| Extra-cellular matrix | itgb4 | integrin, beta 4 | ND | ND | 1.15 | increase |
| Extra-cellular matrix | itga2b | integrin alpha 2b; | 0.50 | increase | 0.15 | no variation |
| Extra-cellular matrix control | timp1 | tissue inhibitor of metalloproteinase 1 | 0.15 | increase | −0.25 | no variation |
| proteoglycan | cspg2 | chondroitin sulfate 2 (versican) | 1.32 | increase | 1.20 | increase |
| Proteoglycan | bgn | biglycan | 2.16 | increase | 0.66 | increase |
| proteoglycan | gpc1 | glypican 1 precursor; | −0.17 | no variation | 0.73 | increase |
| DEJ | nid | nidogen (enactin); | 1.76 | increase | 0.58 | increase |
| DEJ | thbs1 | thrombospondin 1; | ND | ND | 1.52 | increase |

ND: not determined

The PTH (29-32) peptide fragment stimulates the expression of some genes, which belong to different families, such as growth factors (connective tissue growth factor and fibroblast growth factor 2), components of the extra-cellular matrix (collagen I, or many proteoglycans), components of the DEJ (nidogen, thrombospondin). This RNA profile analysis shows that the PTH(29-32) peptide fragment stimulates expression of many fibroblast genes strongly involved in the skin quality.

Example 3

Stimulation of the Synthesis of Lumican on Aged Human Dermal Fibroblasts 3.1. Protocol
Reagents Monoclonal antibody anti-lumican and secondary antibody FITC conjugated were obtained from COGER, Paris.

PBS (Phosphate buffered saline-pH 7.2) and were obtained from SIGMA, L'Isle d'Abeau Chesnes.

IL4 (positive control) was obtained from SIGMA.

Human Dermal Primary Fibroblasts Culture

Human dermal fibroblasts cell suspension were prepared by standard digestion by collagenase of human adult dermis specimens collected from plastic surgery.

After repeated passages (Hayflick model) to mimic ageing in vitro, human dermal fibroblasts were seeded in DMEM for 2 days at 37° C., $CO_2$=5%. Then, acetyl-QDVH (1 and 3 µg/ml) is introduced and after 6 days of incubation at 37° C., $CO_2$=5%, the expression of the lumican synthesis was evaluated on glass slides by immunocytochemistry.

Quantification of the staining was carried out by image analysis.

The results are expressed as the sum of the product of number of pixels by green detected values (arbitrary unit).

3.2 Results

Without treatment, human dermal fibroblasts in culture expressed a small amount of lumican.

The treatment of human dermal fibroblasts with acetyl-Gln-Asp-Val-His (=Acetyl-QDVH) has allowed an increase of lumican expression in the culture.

The treatment by the positive control IL-4, has also induced an increase of lumican expression in the fibroblasts culture.

| | Control without treatment (DMEM) | Treated with IL-4 At 0.1 µg/ml | Treated with Acetyl-QDVH at 1 µg/ml | Treated with Acetyl-QDVH at 3 µg/ml |
|---|---|---|---|---|
| Sum of product of number of pixel by green detected values for lumican (arbitrary unit) | $1\,500\,10^3 \pm 206\,10^3$ | $2\,603\,10^3 \pm 690\pm$ | $2\,488\,10^3 \pm 392\,10^3$ () | $3\,230\,10^3 \pm 490\,10^3$ (*) |

Statistics: mean ± SEM
Test PLSD of Fisher
(**) $p < 0.02$
(***) $p = 0.0001$

These results show that acetyl-QDVH has significantly stimulated the expression of lumican with a dose-dependent effect.

Example 4

Stimulation of the Expression of Collagen Type I Gene Expression from Human Dermal Fibroblasts 4.1. Protocol Reagents Kit for qRT-PCR was obtained from ROCHE (MEYLAN 38242 FRANCE). TGFβ (positive control) was obtained from SIGMA.

Human Dermal Fibroblasts Culture

Human dermal fibroblasts are seeded and incubated for 3 to 5 days at 37° C., $CO_2$=5%.

After exchange of cell culture medium to a defined cell culture medium with the products to be tested, incubation for 1 day at 37° C., $CO_2$=5%. The recovering of cells and numeration before recovering of RNA from human dermal fibroblasts cultured in vitro.

The level of mRNA encoding the collagen type I was evaluated by quantitative RT-PCR or real time RT-PCR.

The results are firstly expressed by the crossing point (CP) which refers to the number of cycle required for the rising of a distinct fluorescence. Then the results of each sample, are calculated as a ratio referring to a reference gene or "house keeping" gene: CP of target/CP of reference gene. EF1α gene was used as internal control gene to normalise the mRNA evaluation.

4.2 Results

|  | Ratio versus calibrator |
|---|---|
| Control medium | 0.75 |
| TGFβ at 10 ng/ml | 2.12 |
| Acetyl-QDVH at 3 µg/ml | 1.05 |
| Acetyl-QDVH at 10 µg/ml | 1.18 |

TGFβ has strongly enhanced the rate of collagen type I gene expression in human dermal fibroblasts. This result validates the assay on cultured fibroblasts.

Acetyl-QDVH peptide has significantly enhanced the rate of collagen type I gene expression in human dermal fibroblasts.

What is claimed is:

1. A cosmetic composition for topical application, comprising: a peptide parathyroid hormone fragment, salts thereof, and combinations thereof, wherein the peptide fragment conforms to the structure

R1-NH-AA-R2 wherein R1 is an acetyl group;

wherein R2 is —OH;

wherein AA corresponds to acids 2-5 of SEQ ID NO:1; and wherein the peptide fragment is present in the composition in an amount effective to cosmetically treat intrinsic or extrinsic deterioration of skin or hair when the composition is topically applied.

2. The composition according to claim 1, wherein AA comprises pGlu-Asp-Val-His (SEQ ID NO:2).

3. The composition according to claim 1, wherein His is replaced by an amino acid selected from the group consisting of Leu, Ile, Nle (Norleucine), Met, Val, Ala, Trp, and Phe.

4. The composition according to claim 1, wherein the peptide fragments are obtained by chemical synthesis, enzymatic synthesis, and controlled hydrolysis of natural proteins of micro-organisms, plants or animals which contain the sequence.

5. The composition according to claim 1, wherein the peptide fragment is present in the composition in an amount effective to combat the formation of wrinkles, reduce the impressions left by wrinkles, strengthen the dermis and/or the dermis/epidermis junction (DEJ), reduce the phenomenon of cellulite of the subcutaneous tissues, promote healing, combat the reduction in the number of cells brought about by deterioration (by ageing or extrinsic factors) of human skin, stimulate and/or regenerate capillary re-growth, and/or combat the loss of hair.

6. The composition according to claim 1, wherein the peptide fragment is present in the composition in an amount effective to stimulate production of the protein TGFI31 (growth transformation factor), the receptors present at the surface of cells which trigger the biological response to TGFI31, mRNA, maternal proteins, proteins involved in the synthesis of dermo-epidermal junction, and combinations thereof.

7. The composition according to claim 1, wherein the peptide fragment is present in the composition in an amount effective to combat inflammation.

8. The composition according to claim 6, wherein the maternal proteins include collagen, elastin, proteoglycans, and combinations thereof.

9. The composition according to claim 6, wherein the proteins involved in the synthesis of dermo-epidermal junction include perlecan, thrombospondin, nidogen, and integrins.

10. The composition according to claim 1, wherein the peptide fragment is present in the composition in an amount effective to regulate the enzymes involved in the degradation of the extra-cellular matrix, for controlling the expression of TIMPs, and combinations thereof.

11. The composition according to claim 1, wherein the peptide parathyroid hormone fragment, salts thereof, and combinations thereof are used at a concentration of from 0.01 to 1000 ppm.

12. A method for treating a substrate against intrinsic or extrinsic cutaneous deterioration, comprising applying the composition according to claim 1 to a substrate selected from skin, human hair, and combinations thereof.

13. The composition according to claim 1, wherein the peptide fragment is present in the composition in an amount effective to increase growth of dermal fibroblasts, increase expression of genes involved in skin quality, increase lumican expression in dermal fibroblasts, and/or increase expression of collagen type I.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Fragment of a parathyroid hormone

<400> SEQUENCE: 1

Leu Gln Asp Val His Asn Phe
1               5

<210> SEQ ID NO 2
<211> LENGTH: 4
<212> TYPE: PRT
<213> ORGANISM: Artificial Sequence
<220> FEATURE:
<223> OTHER INFORMATION: Fragment of a parathyroid hormone

<400> SEQUENCE: 2

Glu Asp Val His
1
```